United States Patent
Hossainy (10) Patent No.: US 9,220,584 B2
(45) Date of Patent: Dec. 29, 2015

(54) TREATMENT OF DIABETIC PATIENTS WITH A STENT AND LOCALLY ADMINISTERED ADJUNCTIVE THERAPY

(75) Inventor: Syed F. A. Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 106 days.

(21) Appl. No.: 13/435,645

(22) Filed: Mar. 30, 2012

(65) Prior Publication Data

US 2013/0261722 A1    Oct. 3, 2013

(51) Int. Cl.
*A61F 2/06*        (2013.01)
*A61F 2/00*        (2006.01)
*A61F 2/958*       (2013.01)

(52) U.S. Cl.
CPC . *A61F 2/00* (2013.01); *A61F 2/958* (2013.01); *A61F 2250/0067* (2013.01)

(58) Field of Classification Search
CPC ............. A61F 2/00; A61F 2/958; A61F 2/91; A61F 2250/0067
USPC ........... 623/1.11, 1.12, 1.23, 1.42, 1.43, 1.44, 623/1.45, 1.46, 1.47, 1.48; 606/192, 194, 606/198; 604/96.01, 101.01–101.05, 604/103.01, 103.02
See application file for complete search history.

(56) References Cited

U.S. PATENT DOCUMENTS

| | | | |
|---|---|---|---|
| 5,049,132 A * | 9/1991 | Shaffer et al. ............ | 604/101.02 |
| 5,091,205 A | 2/1992 | Fan | |
| 5,509,899 A | 4/1996 | Fan et al. | |
| 5,723,269 A | 3/1998 | Akagi et al. | |
| 6,015,815 A | 1/2000 | Mollison | |
| 6,287,588 B1 | 9/2001 | Shih et al. | |
| 6,329,386 B1 | 12/2001 | Mollison | |
| 6,447,835 B1 | 9/2002 | Wang et al. | |
| 6,663,880 B1 * | 12/2003 | Roorda et al. ............... | 424/423 |
| 6,890,546 B2 | 5/2005 | Mollison et al. | |
| 7,399,480 B2 | 7/2008 | Mollison et al. | |
| 7,445,792 B2 | 11/2008 | Toner et al. | |
| 7,758,881 B2 | 7/2010 | Dugan | |
| 7,769,420 B2 | 8/2010 | Silver et al. | |
| 8,048,441 B2 | 11/2011 | Craig et al. | |
| 8,092,822 B2 | 1/2012 | Pacetti et al. | |
| 8,114,968 B2 | 2/2012 | Devy et al. | |

(Continued)

FOREIGN PATENT DOCUMENTS

| | | |
|---|---|---|
| WO | WO 03/037355 | 5/2003 |
| WO | WO 2005/097186 A2 | 10/2005 |
| WO | WO 2008/076847 | 6/2008 |

OTHER PUBLICATIONS

U.S. Appl. No. 10/098,686, filed Mar. 15, 2002, Roorda.

(Continued)

*Primary Examiner* — Katrina Stransky
(74) *Attorney, Agent, or Firm* — Squire Patton Boggs (US) LLP (57) ABSTRACT

Embodiments of the present invention include methods of treating, preventing, and/or ameliorating a vascular disease and/or disorder in a diabetic or pre-diabetic patient. The methods include implanting a stent in a vascular region in a diabetic or pre-diabetic patient, and prior to and/or during the implantation procedure, delivering a lubricant formulation to the vascular region. The stent may be a bare metal stent, or a drug eluting stent, such as a metal stent with a coating including a drug, such as everolimus or sirolimus.

22 Claims, 3 Drawing Sheets

(56) References Cited

U.S. PATENT DOCUMENTS

| | | | |
|---|---|---|---|
| 8,163,269 | B2 | 4/2012 | Carpenter et al. |
| 8,277,868 | B2 | 10/2012 | Kokish et al. |
| 8,367,090 | B2 | 2/2013 | Pacetti et al. |
| 8,431,145 | B2 | 4/2013 | Toner et al. |
| 8,728,510 | B1 | 5/2014 | Roorda |
| 2001/0051166 | A1* | 12/2001 | Luo et al. ............... 424/400 |
| 2002/0037919 | A1 | 3/2002 | Hunter et al. |
| 2003/0144727 | A1 | 7/2003 | Rosenthal et al. |
| 2003/0191179 | A1 | 10/2003 | Joshi-Hangal et al. |
| 2004/0073297 | A1 | 4/2004 | Rohde et al. |
| 2005/0142202 | A1 | 6/2005 | Roorda et al. |
| 2005/0282734 | A1 | 12/2005 | Kadima et al. |
| 2006/0020243 | A1 | 1/2006 | Speck et al. |
| 2006/0045901 | A1 | 3/2006 | Weber et al. |
| 2006/0147489 | A1 | 7/2006 | Shanley et al. |
| 2006/0206149 | A1 | 9/2006 | Yun et al. |
| 2007/0026035 | A1 | 2/2007 | Burke et al. |
| 2007/0083258 | A1 | 4/2007 | Falotico et al. |
| 2007/0224240 | A1 | 9/2007 | Toner et al. |
| 2007/0244549 | A1 | 10/2007 | Pathak et al. |
| 2008/0181927 | A1* | 7/2008 | Zhao ............... 424/423 |
| 2009/0203602 | A1 | 8/2009 | Gelber et al. |
| 2009/0286761 | A1 | 11/2009 | Cheng et al. |
| 2009/0287300 | A1 | 11/2009 | Dave et al. |
| 2010/0030183 | A1* | 2/2010 | Toner et al. ............... 604/500 |
| 2010/0233236 | A1 | 9/2010 | Zhao et al. |
| 2010/0331819 | A1 | 12/2010 | Hossainy et al. |
| 2011/0160575 | A1 | 6/2011 | Beyar et al. |
| 2011/0184384 | A1* | 7/2011 | Davalian et al. ............... 604/509 |
| 2011/0229548 | A1 | 9/2011 | Lim et al. |
| 2011/0275980 | A1 | 11/2011 | Weber et al. |
| 2012/0035150 | A1 | 2/2012 | Gaweco et al. |
| 2012/0122838 | A1 | 5/2012 | Ren et al. |
| 2012/0263759 | A1 | 10/2012 | Hossainy et al. |
| 2013/0224255 | A1 | 8/2013 | Hossainy et al. |
| 2013/0259921 | A1 | 10/2013 | Hossainy |
| 2013/0261723 | A1 | 10/2013 | Stankus et al. |
| 2013/0303496 | A1 | 11/2013 | Cox et al. |

OTHER PUBLICATIONS

U.S. Appl. No. 13/403,709, filed Feb. 23, 2012, Hossainy et al.
U.S. Appl. No. 13/436,303, filed Mar. 30, 2012, Hossainy.
U.S. Appl. No. 13/436,662, filed Mar. 30, 2012, Stankus et al.
U.S. Appl. No. 13/466,504, filed May 8, 2012, Cox et al.
Ajjan et al., "Cardiovascular disease prevention in patients with type 2 diabetes: the role of oral anti-diabetic agents", Diabetes Vasc. Dis. Res. 3, pp. 147-158 (2006).
Berry et al., "Coronary Heart Disease in Patients with Diabetes", J. of the Am. College of Cardiology vol. 49, No. 6, pp. 643-644 (2007).
Cardiovascular disease, downloaded: www.answers.com/topic/cardiovascular-disease, Aug. 12, 2012, 19 pgs.
Cardiovascular disease, downloaded: www.bhf.org.uk/heart-health/conditions/cardiovascular-disease.aspx, Aug. 12, 2012, 2 pgs.
Cardiovascular disease, downloaded: www.wikipedia.org/wiki/Cardiovascular_disease, Aug. 12, 2012, 11 pgs.
Coronary heart diseases, MedlinePlus, downloaded: www.nlm.nih.gov/medlineplus/ency/article, Aug. 12, 2012, 5 pgs.
Definition of Cardiovascular disease. downloaded: www.medterms.com/script/main/art.asp?articlekey, Aug. 12, 2012, 3 pgs.
Hage et al., "Glycaemic control and restenosis after percutaneous coronary interventions in patients with diabetes mellitus: a report from the Insulin Diabetes Angioplasty study", Diabetes & Vascular Disease Res. 6(2) 71-79 (2009).
Hage et al., "The predictive value of inflammatory activity and markers of the adipo-insular axis on restenosis in patients with type 2 diabetes", Diabetes & Vascular Disease Res. 8(2) 143-149 (2011).
Hong et al., "Multiple predictors of coronary restenosis after drug-eluting stent implantation in patiets with diabetes", Heart 92, pp. 1119-1124 (2006).
Letchford, "A review of the formation and classification of amphiphilic block copolymer nanoparticulate structures: micelles, nanospheres, nanocapsules and polymersomes", EU J. of Pharm. and biopharmaceutics vol. 65, issue 3, pp. 259-269 (2007).
Libby "Inflammation and cardiovascular disease mechanisms", Am. J. Clin. Nutr. 83 suppl. pp. 456S-460S (2006).
Libby et al., "Inflammation in Diabetes Melltus: Role of Peroxisome Proliferator-Activated Receptor-$\alpha$ and Peroxisome Proliferator-Activated Receptor-$\gamma$ Agonists", The Am. J. of Card. vol. 99 (4A) pp. 27B-28B (2007).
Nissen "Pioglitazone to Reduce Restenosis After Bare-Metal Stent Placement?", JACC vol. 2, No. 6, pp. 532-533 (2009).
Opsteen et al., "Block copolymer vesicles", Pure Appl. Chem. vol. 76, No. 7-8, pp. 1309-1319 (2004).
Philpott et al., "Long-term outcomes of patients receiving drug-eluting stents", CMAJ 180 (2) pp. 167-168 (2009).
Shan et al., "Leptin-enhanced neointimal hyperplasia is reduced by mTOR and P13K inhibitors", PNAS vol. 105, No. 48 pp. 19006-19011 (2008).
Sobel "Acceleration of Restenosis by Diabetes, Pathogenetic Implications", J. of the Am. Heart Assoc., Circulation 103, pp. 1185-1187 (2101).
Ta-Jen Liu et al., "NVP-BEZ235, a novel dual prhosphatidylinositol 3-kinase/mammalian target of rapamycin inhibitor, elicits multifaceted antitumor activities in human gliomas", Mol. Cncer Ther. 8(8), pp. 2204- (2009).
Takagi et al., "A prospective, Multicenter, Randomized Trial to Assess Efficacy of Pioglitazone on In-Stent Neointimal Suppression in Type 2 Diabetes", JACC Cardiovascular Interventions vol. 2, No. 6, pp. 524-531 (2009).
The Heart and Vascular Disease. downloaded: www.medicinenet.com/vascular_disease/article.htm, Aug. 12, 2012, 4 pgs.
Vascular disease, downloaded: www.wikipedia.org/wiki/Vascular_disease, Aug. 12, 2012, 3 pgs.
What is a vascular disease? downloaded: www.clevelandclinic.org/heart/disorders/vascular/whatis.aspx, Aug. 12, 2012, 4 pgs.
What is Cardiovascular disease (Heart Disease)? Downloaded: www.heart.org/HEARTORG/Caregiver/Resources/WhatisCardiovascularDisease/W, Aug. 12, 2012, 2 pgs.
What is Cardiovascular disease? downloaded: www.news-medical.net/health/What-is-Cardiovascular-disease.aspx, Aug. 12, 2012, 3 pgs.
"Diagnosis and Classification of Diabetes Mellitus", Diabetes Care vol. 27, No. suppl. 1, pp. S5-S10 (2004).
"Diagnosis of Diabetes and Prediabetes", National Diabetes Information Clearinghouse (NDIC), downloaded from: www.diabetes.niddk.nih.gov/dm/pubs/diagnosis/, Feb. 1, 2013 11 pgs.
"Heart Disease", American Diabetes Association, downloaded from: www.diabetes.org/living-with-diabetes/complications/heart-disease, Jan. 31, 2013, 2 pgs.
Jackson Behan, "New ADA Guidelines for Diagnosis, Screening of Diabetes", Advance Laboratory vol. 20, issue 1, downloaded from: www.laboratory-manager.advanceweb.com/Archives/Article-Archives/New-ADA-Gudelin. Feb. 1, 2013, 4 pgs.
The Procedure: What to Expect—Getting a Stent, Medtronic, Sep. 22, 2010, pp. 1-2.
"PTCA or Angioplasty," HeartSite.com, Aug. 8, 2002, pp. 1-3.
Ghosh, S., et al., "Skin Permeation of Rosiglitazone from Transdermal Matrix Patches," *Pharmaceutical Technology*, vol. 34, Issue 5 (May 2, 2010), 7 pages.

* cited by examiner

TREATMENT OF DIABETIC PATIENTS WITH A STENT AND LOCALLY ADMINISTERED ADJUNCTIVE THERAPY

BACKGROUND OF THE INVENTION

1. Field of the Invention

This invention relates to methods of treating vascular diseases and disorders in diabetic and pre-diabetic patients.

2. Description of the State of the Art

Until the mid-1980s, the accepted treatment for coronary atherosclerosis, i.e., narrowing of the coronary artery(ies) was coronary by-pass surgery. While being quite effective and having evolved to a relatively high degree of safety for such an invasive procedure, by-pass surgery still involves potentially serious complications and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The re-opening of the artery by an inflatable balloon is also referred to as "dilatation" of the artery. The procedure was relatively non-invasive, took a very short time compared to by-pass surgery, and the recovery time was minimal. However, PTCA brought with it other problems such as vasospasm and elastic recoil of the stretched arterial wall which could undo much of what was accomplished and, in addition, created a new problem, restenosis, the re-clogging of the treated artery due to neointimal hyperplasia.

The next improvement, advanced in the mid-1980s, was the use of a stent to maintain the luminal diameter after PTCA. This for all intents and purposes put an end to vasospasm and elastic recoil but did not entirely resolve the issue of restenosis. That is, prior to the introduction of stents, restenosis occurred in from about 30 to 50% of patients undergoing PTCA. Stenting reduced this to about 15 to 20%, a substantial improvement but still more restenosis than desirable. For diabetic patients, however, the incidence of restenosis as well as major cardiac events are significantly higher than non-diabetics patients with stenting.

In 2003, drug-eluting stents or DESs were introduced. The drugs employed with the DES are cytostatic compounds, that is, compounds that curtail the proliferation of cells that resulted in restenosis. The occurrence of restenosis has been reduced to about 5 to 7%, a very improved figure. However, based upon the studies to date, the rate of restenosis with DES is still higher for diabetic patients than non-diabetic patients. Thus, there is a need for improved methods for treating vascular diseases and disorders in diabetic and pre-diabetic patients.

SUMMARY OF THE INVENTION

The present invention is directed to methods of treating vascular diseases and disorders in diabetic and pre-diabetic patients. The methods involve the implantation of a stent.

Various embodiments of the present invention include methods of treating, preventing, or ameliorating a vascular disease and/or disorder in a diabetic or pre-diabetic patient. The methods include, but are not limited to, delivering a stent to, and deploying the stent at, a vascular region of a patient, and prior to, during, or both prior to and during the deployment of the stent, administering (delivering) a lubricant formulation to the vascular region of the patient. The patient may be identified as having a diabetic condition or a pre-diabetic condition, and the patient may be in need of treating, preventing, or ameliorating a vascular disease and/or disorder.

In the various embodiments, the lubricant formulation may be administered through a catheter, through an array of holes in a catheter, or both. The catheter may optionally be used for the delivery and deployment of the stent. The release of the lubricant formulation from the catheter may occur when the stent is ready to deploy but before the stent is actually deployed, during the deployment of the stent, or when the stent is ready to deploy and during the deployment of the stent.

In an aspect of the invention, the lubricant formulation may be administered by release from the middle section of a dual balloon or from the smaller diameter of a balloon having substantially two diameters, where the stent may be also mounted on the balloon and may be deployed simultaneously with the balloon inflation and lubricant formulation release. In a further aspect, the stent may be mounted in the middle section or the section having the smaller of the two diameters.

In an aspect of the invention, the lubricant formulation may be administered by a balloon used prior to dilatation of the vascular region, and the stent may be delivered by a stent delivery system which does not include the pre-dilation balloon.

In an aspect of the invention, the lubricant formulation may be administered by a catheter balloon, and the stent may be mounted on at least a portion of the length of the catheter balloon, and the lubricant formulation may be disposed over the entire length, or substantially the entire length, of the balloon.

In a further aspect, the lubricant formulation may also be disposed over at least a portion of the mounted stent.

In an aspect of the invention, the lubricant formulation may consist essentially of or may include, but is not limited to, a water miscible polymer, a water soluble oligomer, a biopolymer, a biomolecule, or a combination thereof.

In an aspect of the invention, the lubricant formulation may include, but is not limited to, at least one of the following: carboxymethylcellulose, hyaluronic acid, polyvinylpyrrolidone, polyethylene glycol, polyethylene oxide, and heparin.

In an aspect of the invention, the lubricant formulation may include, but is not limited to, at least one surfactant.

In an aspect of the invention, the surfactant may be selected from the following: diblock copolymers and co-oligomers of polyethylene oxide-co-polypropylene oxide, triblock copolymers of polyethylene oxide-co-polypropylene oxide, polyvinyl alcohol, polysorbate 20, polysorbate 60, polysorbate 80, and polyethylene glycol p-(1,1,3,3-tetramethylbutyl)-phenyl ether (Triton X-100), palmitate-co-polyethylene glycol, and combinations thereof.

In an aspect of the invention the lubricant formulation may include a solvent.

In an aspect of the invention, the solvent may be selected from the following: water, normal saline solution, n-methyl-2-pyrrolidone, 2-pyrrolidone, propylene glycol, ethanol, glycerin, and combinations thereof.

In an aspect of the invention, the solvent may be a substance that is a semi-solid or liquid at about 37° C.

In an aspect of the invention, the lubricant formulation is administered proximal to the vascular region to be treated, at the vascular region to be treated, or both proximal to and at the vascular region to be treated. The vascular region to be treated may also be referred to as the stented segment or stented region once the stent has been implanted.

DETAILED DESCRIPTION OF THE INVENTION

Use of the term "herein" encompasses the specification, the abstract, and the claims of the present application.

Use of the singular herein includes the plural and vice versa unless expressly stated to be otherwise, or obvious from the context that such is not intended. That is, "a" and "the" refer to one or more of whatever the word modifies. For example, "a drug" includes one drug, two drugs, etc. Likewise, "the polymer" may refer to one, two or more polymers, and "the device" may mean one device or a plurality of devices. By the same token, words such as, without limitation, "polymers" and "devices" would refer to one polymer or device as well as to a plurality of polymers or devices unless, again, it is expressly stated or obvious from the context that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. In general, but with the preceding discussion in mind, a numerical value herein that is modified by a word of approximation may vary from the stated value by ±15%, unless expressly stated otherwise.

As used herein, any ranges presented are inclusive of the end-points. For example, "a duration of time between 10 and 75 minutes" or "a duration of time from 10 to 75 minutes" includes 10 minutes and 75 minutes, as well as any specific duration of time in between 10 minutes and 75 minutes.

As used herein, a "drug" refers to a substance that, when administered in a therapeutically effective amount to a patient suffering from a disease, disorder, or condition, has a therapeutic beneficial effect on the health and well-being of the patient. A therapeutic beneficial effect on the health and well-being of a patient includes, but is not limited to: (1) curing the disease, disorder, or condition; (2) slowing the progress of the disease, disorder, or condition; (3) causing the disease, disorder, or condition to retrogress or to be in remission; or, (4) alleviating, ameliorating or both alleviating and ameliorating one or more symptoms of the disease, disorder, or condition.

As used herein, a "drug" also includes any substance that when administered to a patient, known or suspected of being particularly susceptible to a disease, disorder, or condition, in a prophylactically effective amount, has a prophylactic beneficial effect on the health and well-being of the patient. A prophylactic beneficial effect on the health and well-being of a patient includes, but is not limited to: (1) preventing or delaying on-set of the disease, disorder, or condition in the first place; (2) maintaining a disease, disorder, or condition at a retrogressed level once such level has been achieved by a therapeutically effective amount of a substance, which may be the same as or different from the substance used in a prophylactically effective amount; or, (3) preventing or delaying recurrence of the disease, disorder, or condition after a course of treatment with a therapeutically effective amount of a substance, which may be the same as or different from the substance used in a prophylactically effective amount, has concluded.

As used herein, "drug" also refers to pharmaceutically acceptable, pharmacologically active derivatives of those drugs specifically mentioned herein, including, but not limited to, salts, esters, amides, hydrates, solvates, and the like.

As used herein, the phrase "drug is X" refers also to pharmaceutically acceptable, pharmacologically active derivatives of the drug X, such as, but not limited to, salts, esters, amides, hydrates, solvates, and the like. As a non-limiting an example, "the drug is dexamethasone" would also encompass dexamethasone acetate.

As used herein, a "polymer" refers to a molecule comprised of repeating "constitutional units." The constitutional units derive from the reaction of monomers. The constitutional units themselves can be the product of the reactions of other compounds. As a non-limiting example, ethylene ($CH_2=CH_2$) is a monomer that can be polymerized to form polyethylene, $CH_3CH_2(CH_2CH_2)_nCH_2CH_3$ (where n is an integer), wherein the constitutional unit is —$CH_2CH_2$—, ethylene having lost the double bond as the result of the polymerization reaction. A polymer may be derived from the polymerization of two or more different monomers and therefore may comprise two or more different constitutional units. Such polymers are referred to as "copolymers." "Terpolymers" are a subset of "copolymers" in which there are three different constitutional units. Those skilled in the art, given a particular polymer, will readily recognize the constitutional units of that polymer and will readily recognize the structure of the monomer from which the constitutional units derive. Polymers may be straight chain, branched chain, star-like or dendritic. One polymer may be attached (grafted) onto another polymer. The constitutional units of polymers may be randomly disposed along the polymer chain, may be present as discrete blocks, may be so disposed as to form gradients of concentration along the polymer chain, or a combination thereof. Polymers may be cross-linked to form a network.

As used herein, a polymer has a chain length of 50 constitutional units or more, and those compounds with a chain length of fewer than 50 constitutional units are referred to as "oligomers."

As used herein, a "solvent" refers to a substance capable of dissolving, partially dissolving, dispersing, suspending, or any combination thereof, a substance to form a uniform dispersion, solution, or suspension, with or without agitation, at a selected temperature and pressure. The substance may be a solid, semi-solid, a liquid, a gas, or a supercritical fluid. A solvent herein may be a blend of two or more such substances.

A "normal saline solution," is a saline solution that is essentially isotonic with blood. Saline solutions are those that contain a salt or salts, typically sodium chloride.

A "fluid," as defined by Merriam Webster dictionary, is a substance that tends to flow or conform to the outline of its container. A fluid is a state of matter that includes gases, liquids, supercritical fluids, and plasma. As used herein, a fluid can be a substance that would conform to the shape of its container within a time frame of about 5 or 10 minutes (up to an hour) under the force of gravity.

A "semi-solid" as defined by Merriam Webster dictionary is "a substance having qualities of both a solid and a liquid; highly viscous." As used herein, a semi-solid can be a substance that would conform to the shape of its container under high stress, or in the absence of stress, by gravity, over a long period of time (at least 8 hours, but potentially days or weeks). In contrast, a "solid" as defined by the Merriam Webster dictionary, is a substance that does not flow perceptibly under moderate stress, has "a definite capacity for resisting forces" such as compression or tension "which tend to deform it," and "under ordinary conditions retains a definite shape and size." A solid may conform to the outline of its container by breaking chemical bonds, by the application of extensive deformation, or a combination thereof. Elastic solids may conform to the shape of a container with the application of stress, but then return to its prior shape, or substantially its prior shape, when the stress is removed.

As used herein, the terms "biodegradable," "bioerodable," "bioabsorbable," "degraded," "eroded," "absorbed," and "dissolved," are used interchangeably, and refer to a substance that is capable of being completely or substantially, degraded, dissolved, eroded, or any combination thereof, over time when exposed to physiological conditions (pH, temperature, enzymes and the like), and can be gradually eliminated by the body, or that can be degraded into fragments that can pass through the kidneys. Conversely, "biostable" refers to a substance that is not biodegradable, etc.

As used herein, a material that is described as a layer, a film, or a coating "disposed over" a substrate refers to deposition of the material directly or indirectly over at least a portion of the surface of that substrate. "Directly deposited" means that the material is applied directly to the surface of the substrate. "Indirectly deposited" means that the material is applied to an intervening layer that has been deposited directly or indirectly over the substrate. The terms "layer," "film," and "coating" are used interchangeably herein. A coating may have multiple layers, and each layer may be applied by multiple applications of coating material. Layers typically differ from each other in the type of materials, the ratio of materials, or both the type of and the ratio of materials applied to form the layer. Materials may migrate from one layer to another layer during the coating application process, after the coating has been formed or both during the coating application process and after the coating has been formed.

As used herein, a "hole" is an opening or a channel in a material created by any one or more of a combination of etching, laser machining, mechanical machining, drilling, and conventional processes known by persons of ordinary skill in the art. The location of holes may be predetermined.

As used herein, a "pore" is an opening or channel in a material that naturally results from the properties of the material. The location of pores may not be pre-determined.

As used herein, the terms "pores" and "holes" will be used interchangeably unless expressly stated otherwise.

As used herein, a "cardiovascular disease" is a disease, condition, or disorder that impacts the heart, circulatory system, or both the heart and the circulatory system. The circulatory system is the lymphatic system and the cardiovascular system. The lymphatic system distributes lymph. The cardiovascular system is a system of blood vessels, primarily arteries and veins, which transport blood to and from the heart, brain and peripheral organs such as, without limitation, the arms, legs, kidneys and liver. The coronary system supplies blood to and from the heart and includes the coronary artery system which supplies blood to the heart. The carotid system supplies blood to and from the brain and includes the carotid artery system which supplies blood to the brain. The peripheral vascular system carries blood to (primarily via arteries) and from (primarily via veins) the peripheral organs such as, without limitation, the hands, legs, kidneys and liver. The coronary system, carotid system, and the peripheral vascular system are part of the cardiovascular system.

As used herein, a "vascular disease" refers to a disease, condition, or disorder that impacts the circulatory system. In particular "vascular disease" includes a disease, disorder, or condition of the coronary system, the carotid system, and/or the peripheral vascular system.

"Vascular diseases" are a subset of "cardiovascular diseases."

Examples of cardiovascular diseases include diseases of the heart which include, but are not limited to, heart valve disease, arrhythmia, heart failure, and congenital heart disease, and vascular diseases, which include, but are not limited to atherosclerosis, thrombosis, restenosis, hemorrhage, vascular dissection or perforation, vulnerable plaque, chronic total occlusion, claudication, anastomotic proliferation for vein and artificial grafts, peripheral artery disease, carotid artery disease, coronary artery disease, anuerysm, renal (kidney) artery disease, raynaud's disease, buerger's disease (a.k.a. thromboangiitis obliterans), peripheral venous disease, varicose veins, blood clots in the veins, blood clotting disorders, and lymphdema.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, vascular grafts, self-expandable stents, balloon-expandable stents, and stent-grafts.

With respect to an implantable medical device, the "outer surface" is meant any surface however spatially oriented that is in contact with bodily tissue or fluids.

With respect to an implantable medical device, a "device body" refers to an implantable medical device in a fully formed utilitarian state with an outer surface to which no coating or layer of material different from that of which the device itself is manufactured has been applied.

One type of implantable medical device is a stent. Stents are implantable medical devices that are generally cylindrically shaped, and function to hold open, and sometimes expand, a segment of a blood vessel or other lumen or vessel in a patient's body when the vessel is narrowed or closed due to diseases, conditions, or disorders including, but not limited to, coronary artery disease, carotid artery disease and peripheral arterial disease. A stent can be used in, without limitation, neuro, carotid, coronary, pulmonary, renal, biliary, iliac, femoral and popliteal, and other peripheral vasculatures, as well as other bodily lumens. A stent can be used in the treatment or prevention of cardiovascular diseases and disorders, as well as other diseases and disorders. For a stent, the "outer surface" includes the luminal surface which faces the lumen interior, the abluminal surface which faces the lumen wall, and sidewall surfaces, if present, which connect the abluminal and luminal surfaces.

A bare metal stent (BMS), which, as the name implies, is a fully-formed usable stent that has not been coated with a layer of any material different from the metal of which it is made on any surface that is in contact with bodily tissue or fluids. Similarly, stents may be formed from other materials, or a combination of other materials and a polymer, and not have any coatings disposed over the outer surface.

Another category of medical devices are insertable medical devices. "Insertable medical devices" include any type of appliance that is totally or partly introduced, surgically or medically, into a patient's body or by medical intervention into a natural orifice, but the device does not remain in the patient's body after the procedure.

A "catheter" is a thin, flexible tube for insertion into a natural body cavity, duct, or vessel, to introduce or remove fluid, to distend the vessel, or to hold open the vessel or cavity. Catheters may be insertable devices, or may be implanted for several hours or days.

A "vascular catheter" is an insertable medical device. A vascular catheter is a thin, flexible tube with a manipulating means at one end, which remains outside the patient's body, and an operative device at or near the other end, which is inserted into the patient's artery or vein. The catheter may be used for the introduction of fluids, often containing drugs, to the target site. The catheter may be used to deliver a stent to the target site, or may be used to deliver a balloon used in angioplasty. The catheter may perform multiple functions.

As used herein, a "balloon" comprises a relatively thin, flexible material, forming a tubular membrane, and is usually associated with a vascular catheter. When positioned at a particular location in a patient's vessel, it can be expanded or inflated to an outside diameter that is essentially the same as the inside or luminal diameter of the vessel in which it is placed. Balloons may be inflated using a liquid medium such as water or normal saline solution. Non-limiting examples of suitable balloon materials include polyester, PEBAX® (polyether block amide block copolymers, Arkema), polyurethanes, poly(tetra-fluoroethylene) (aka PTFE, and TEFLON®, DuPont Co., Wilmington, De.), nylon, and DACRON® (DuPont Co.).

A "balloon catheter" refers to a medical device which is a system of a catheter with a balloon at the end of the catheter.

A "balloon" of a "balloon catheter" may be used to perform one or more of the following functions: dilate a vessel ("a dilatation balloon"); deliver a drug and/or another substance to a vessel; and expand a stent that has been mounted over the balloon.

Figure 1:
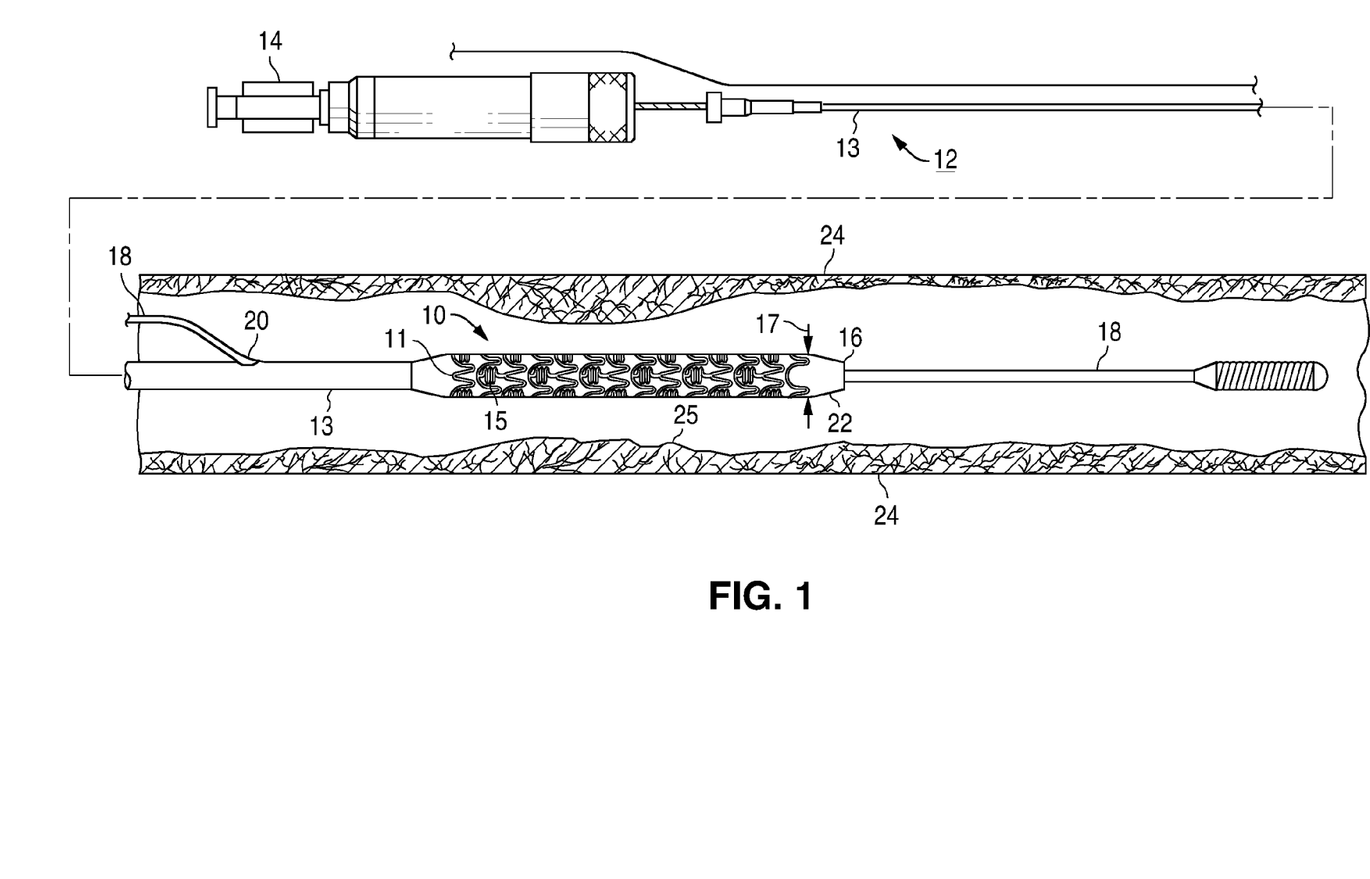
FIG. 1 is an elevational view, partially in section, of a typical stent mounted on a delivery catheter and disposed within a damaged artery.

A typical implantation of a stent is described in the following paragraphs. FIG. 1 generally depicts a stent 10, mounted on a catheter assembly 12 which is used to deliver the stent 10 and implant it in a body lumen, such as a blood vessel 24. The non-limiting example of a stent 10 that is shown in FIG. 1 comprises a plurality of radially expandable cylindrical rings 11 disposed generally coaxially and interconnected by undulating links 15 disposed between adjacent cylindrical rings 11. The combination of cylindrical rings 11 and links 15 form the stent body, that is the device body of the stent (also referred to as the scaffolding), which supports the vessel once deployed. The catheter assembly 12 includes a catheter shaft 13 which has two ends, a first end 14 and a second end 16. The catheter assembly 12 is configured to advance through the patient's vascular system by advancing over a guide wire by any of the well known methods, including a rapid exchange catheter system, such as the one shown in FIG. 1. Another well known method for stent delivery is an over the wire system.

Catheter assembly 12 as depicted in FIG. 1 is of the well-known rapid exchange type which includes an RX port 20 where the guide wire 18 will exit the catheter from a lumen, which is a passageway or cavity, in the shaft 13. The distal end of the guide wire 18 exits the catheter second end 16 so that the catheter advances along the guide wire on a section of the catheter between the RX port 20 and the catheter second end 16. If the stent is of the balloon-expandable type, the stent is mounted on a balloon 22 and is crimped tightly thereon so that the stent 10 and balloon 22 present a low profile diameter for delivery through the arteries. Alternatively, a self-expanding stent configuration as is well known in the art may be used.

Figure 2:
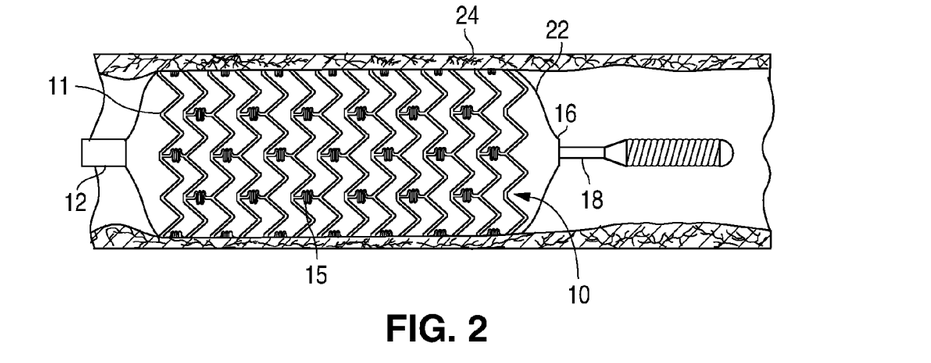
FIG. 2 is an elevational view, partially in section, similar to that shown in FIG. 1 wherein the stent is expanded within a damaged artery.
Figure 3:
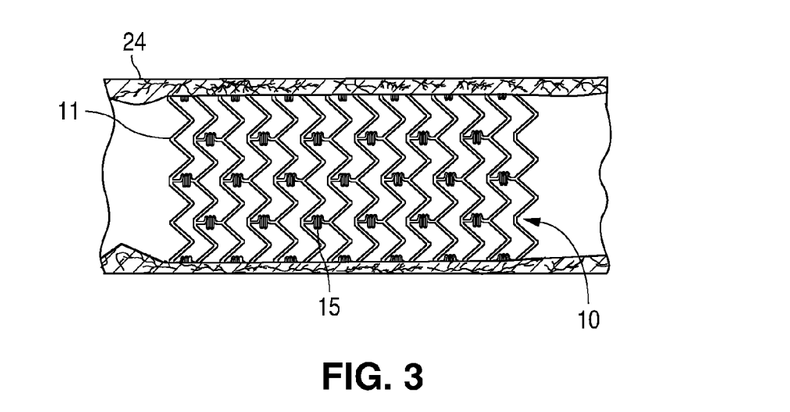
FIG. 3 is an elevational view, partially in section, depicting the expanded stent within the artery after withdrawal of the delivery catheter.

As shown in FIG. 1, a partial cross-section of an artery 24 is shown with a small amount of plaque 25 that has been previously treated by a repair procedure. A stent 10 may be used to repair a diseased or damaged arterial wall which may include the plaque 25 as shown in FIG. 1, or a dissection, or a flap which are commonly found in the coronary arteries, carotid arteries, peripheral arteries and other vessels. In a typical procedure to implant stent 10, the guide wire 18 is advanced through the patient's vascular system by well known methods so that the distal end of the guide wire is advanced past the plaque or diseased area 25. The introduction of the stent into the body and transport to a region that is to be treated is referred to herein as "delivery." Once the stent 10 has been delivered to the region to be treated, the stent delivery catheter assembly 12 is advanced over the guide wire so that the stent 10 is positioned in the target area. The balloon 22 is inflated by well known means so that it expands radially outwardly and in turn expands the stent 10 radially outwardly until the stent is apposed to the vessel wall. The radial expansion of the stent, by a balloon or otherwise, until the stent is apposed to the vessel wall is referred to herein as "deployment" of the stent. The balloon 22 is then deflated and the catheter withdrawn from the patient's vascular system. The guide wire 18 typically is left in the lumen for post-stent implantation procedures, if any, and subsequently is withdrawn from the patient's vascular system. A lumen in the catheter shaft 13 may be used to deliver fluids, potentially including a drug, to the site, such as the site of plaque 25. As depicted in FIGS. 2 and 3, the balloon 22 is fully inflated with the stent 10 expanded and pressed against the vessel wall, and in FIG. 3, the implanted stent 10 remains in the vessel after the balloon 22 has been deflated and the catheter assembly 12 and guide wire 18 have been withdrawn from the patient. As used herein, "implantation" of a stent refers to the delivery and deployment of the stent.

As obvious form the preceding discussion, a balloon, a catheter, and a stent perform different functions. A stent may be and is typically crimped to a smaller diameter for delivery, and then the stent may be subsequently deployed by being allowed to expand if self-expanding, or is expanded by a balloon or other device, to a large diameter. The expanded stent is capable of supporting a bodily lumen for an extended period of time. In contrast, a balloon has a wall thickness that is so thin that the tubular membrane cannot support a load at a given diameter unless inflated with a fluid. Furthermore, a balloon is a transitory device that is inserted in the patient's body for only a limited time for the purpose of performing a specific procedure or function. Dilatation balloons used to expand a vessel wall, and optionally open an occluded vessel, are not implanted, but are removed from the body at the end of the procedure. Catheters have a shaft which is similar to a stent in that most stents and catheter shafts are tubular or cylindrical in shape. However, a catheter shaft is not designed to be radially expandable. In addition, a vascular catheter has a much larger (a factor of 10 or greater) length to diameter ratio than a stent.

As discussed previously, the use of stents has reduced the incidence of restenosis, but to a lower extent in diabetic patients. As an example, one study found that after a percutaneous cardiac intervention, such as PTCA, followed by the implantation of a BMS, the rate of restenosis was 30% for diabetic patients compared to 20% for non-diabetic patients. Another study involving implantation of a DES, found a rate of 14.6% restenosis in non-diabetics, but 20.9% for diabetic patients. In addition, diabetic patients are more likely to experience major adverse cardiac events (MACE) after PTCA with stenting.

Diabetes, and even hyperglycemia, independent of whether or not a person has been diagnosed with diabetes, is a risk-factor for cardiovascular events. In general, diabetics are more than twice as likely as non-diabetics to have a heart attack or stroke, and 2 out of 3 diabetics die from cardiovascular disease (American Diabetes Association).

Diabetic patients are those individuals suffering from diabetes mellitus, often referred to as just "diabetes," a group of metabolic diseases. Diabetes may be type 1, previously referred to as juvenile diabetes, in which an individual is unable to produce insulin. Type 1 diabetes may also be called insulin dependent diabetes. Type 2 diabetes results from an insulin level which is too low, or an inability to utilize insulin, referred to as "insulin resistance." As used herein, a person may be diagnosed as diabetic if at least one of the following applies:
 (1) fasting plasma glucose level is greater than or equal to 7.6 mmol/L (126 mg/dL);
 (2) plasma glucose level is greater than or equal to 11.0 mmol/L (200 mg/dL) 2 hours after a 75 gram oral glucose load (standard glucose tolerance test);
 (3) symptoms of hyperglycemia (described below), and a "casual" plasma glucose of greater than or equal to 11.1 mmol/L;
 (4) glycated hemoglobin (a.k.a. hemoglobin A1C or HbA1C) of greater than or equal to 6.5%.

In general, the measurements may be and preferably are repeated on more than one day for a definitive diagnosis of diabetes. Hyperglycemia is a condition of high plasma glucose. Symptoms of hyperglycemia include increased thirst and urination, increased hunger, blurred vision, feelings of weakness, weight loss, and dry mouth. Those people in which at least one of the following apply, (1) a fasting blood glucose that is 5.6 to 6.9 mmol/liter (100 to 125 mg/dL), and (2) a glucose tolerance test plasma glucose level of 7.8 to 11.1 mmol/liter (140 to 200 mg/dL), are classified as "pre-diabetic."

As used herein, a "diabetic patient" is an individual (animal, including human) who has been diagnosed as having diabetes, either type 1 or type 2, or an individual, although not diagnosed as diabetic, who would be diagnosed as a diabetic individual if that individual were to be evaluated. As an example, for a human, if the plasma glucose or HbA1C, if measured, would fall within the range described above that is classified as diabetic, that individual would be classified as a "diabetic patient," even if not formally diagnosed. Different criteria may apply to individuals of different species. The methods of the present invention encompass treatment of those individuals classified as diabetic under current clinical criteria, as well as those who classify as diabetic under any criteria as revised or developed in the future. Those referred to as "pre-diabetic" individuals would be determined analogously.

It is believed that there are a number of reasons that diabetics exhibit higher rates of cardiovascular disease, including vascular diseases. Diabetics suffer from endothelial dysfunction making diabetics more prone to vascular lesions. The high blood glucose levels may damage heart muscle, and increase oxidative stress. Many diabetic patients have "atherogenic dyslipidemia," or an abnormal lipid profile in the blood. This abnormal lipid profile is characterized by elevated triglycerides, and low levels of high density lipoprotein (HDL) cholesterol. Even if the low density lipoprotein (LDL) cholesterol, also referred to as "bad cholesterol," is at a normal level, the actual LDL particles are often abnormal, such as smaller, denser, or both smaller and denser, and as a result of these abnormalities, are more likely to lead to atherosclerosis. Inflammation also plays a role in the development of diabetes, and plasma levels of inflammatory molecules and adhesion molecules are elevated in diabetic patients. Some experts have referred to type II diabetes as a "chronic inflammatory disease." At least one study has found a correlation between blood markers of inflammation and the propensity to become diabetic, but the correlation was not applicable to African Americans and smokers. Animal models have shown that T cells and macrophages, both involved in immune response, are involved in the development of diabetes, insulin resistance, or both.

Vascular diseases may also involve inflammatory processes. It is believed that the atherosclerosis plaque formation initiates with the stimulation of VCAM-1 (vascular cell adhesion molecule-1) by endothelial cells in the wall of the artery. "Atherosclerosis" refers to the depositing of fatty substances, cholesterol, cellular waste products, calcium and fibrin on the inner lining, or intima, of an artery. Smooth muscle cell proliferation and lipid accumulation accompany the deposition process. Stimulation of VCAM-1 is thought to occur by oxidized lipids. Another pathway for stimulation of VCAM-1 involves nuclear factor-κB. VCAM-1 may also be stimulated by proinflammatory cytokines. Cytokines are small cell-signaling proteins. An example of a proinflammatory cytokine that may stimulate VCAM-1 is IL-1β, interluenkin-1β. VCAM-1 may also be stimulated by a substance called TNF-α, tumor necrosis factor-α. Specifically, the stimulation of VCAM-1 results in the adhesion of white blood cells, including immune modulated white blood cells. The white blood cells within the vessel wall eventually become macrophages, which are involved in immune response by engulfing and digesting cellular debris and pathogens. In the development of atherosclerosis, the macrophages engulf modified lipoproteins in the blood, particularly LDL. In a cascade effect, the macrophages also produce growth factors and cytokines, which are proinflammatory, thus attracting more white blood cells. Eventually the macrophages become the foam cells seen in atherosclerotic plaque.

Atherosclerotic plaque, also called fibrous (atheromatous) plaque and an atherosclerotic lesion, result from the accumulation of substances on the intima and occlude the lumen of the artery, a process called stenosis. When the stenosis becomes severe enough, the blood supply to the organ supplied by the particular artery is depleted resulting in a stroke, if the afflicted artery is a carotid artery, a heart attack if the artery is a coronary artery, or a loss of organ function if the artery is peripheral.

Stenting and PTCA can injure the vessel wall, such as by causing endothelial denudation, and the injury may cause inflammation. Inflammation may result in changes to smooth muscle cells, with over-proliferation of muscle cells and migration of these cells into the intima. It is the overgrowth of cells that may lead to restenosis. Thus, the vascular injury caused by stenting may eventually lead to restenosis.

Embodiments of the present invention include methods of treating, preventing, or ameliorating a vascular disease and/or disorder in a diabetic or pre-diabetic patient who is in need of treating, preventing, or ameliorating a vascular disease and/or disorder, and who may be identified as having a diabetic condition or a pre-diabetic condition. The methods include delivery of a stent to a vascular region in the patient and deployment of the stent at the vascular region of the patient, and administering a lubricant formulation to the vascular region prior to, during, or both prior to and during the deployment of the stent. In some embodiments, the patient is identified as having a diabetic condition or a pre-diabetic condition.

Vascular regions or sites that may benefit from treatment include, but are not limited to, vascular lesions, atherosclerotic lesions, site of vulnerable plaque(s), and the site of a peripheral arterial disease. A peripheral artery disease site may be an atherosclerotic lesion in a peripheral artery that is also caused by the buildup of fatty deposits on the lining or intima of the artery walls. Examples of vascular lesions include, without limitation, saphenous vein graft lesions, restenotic lesions, bifurcation lesions, ostial lesions, left main lesions, chronic total occlusions and occlusions associated with AMI (Acute Myocardial Infarction), and STEMI (ST-segment Elevation Myocardial Infarction).

"Vulnerable plaque" refers to an atheromatous plaque that has the potential of causing a thrombotic event (formation of a clot within the vessel that blocks the vessel), and is usually characterized by a very thin wall separating it from the lumen of an artery. The thinness of the wall renders the plaque susceptible to rupture. The walls are formed from collagen which may be negatively impacted by inflammation as well as other substances present in the blood stream. When the plaque ruptures, the inner core of usually lipid-rich plaque is exposed to blood, with the potential of causing a fatal thrombotic event through adhesion and activation of platelets and plasma proteins to components of the exposed plaque.

In embodiments of the present invention, the lubricant formulation may be administered locally to the vascular region of the patient. The local administration may be intra-arterial such as by a balloon, a balloon catheter, a catheter, a guide catheter (a catheter which is delivered proximal to a region to be treated in a lumen, such as a blood vessel, and through which other devices, such as, without limitation, a balloon catheter used in angioplasty, are delivered to the region of the lumen to be treated), a micro-catheter (a catheter for use in smaller diameter vasculature or lumens). Other means of local administration may also be used and some of these are discussed in more detail below.

It is believed that the application of a lubricant formulation to a vessel wall prior to the implantation of the stent, or prior to the deployment of stent may reduce the mechanical injury to the vessel wall. It is believed that the lubricant formulation may prevent, ameliorate, or reduce endothelial denudation, and as a result, inflammation, at the site of stenting.

A lubricant is generally a substance which reduces friction, and particularly reduces friction between moving parts. A lubricant is slippery. As used herein, a "lubricant formulation" is a substance, or a mixture of substances, which reduces friction of a surface when disposed over at least a portion of the surface. The lubricant formulation may be a fluid. The lubricant formulation may be a semi-solid.

In some embodiments, the lubricant formulation includes, but is not limited to, a material, such as, without limitation, a polymer, an oligomer, or a combination thereof, and the material may optionally be dissolved, dispersed, or both dissolved and dispersed in a solvent. The solvent may be water or a normal saline solution. Other fluids may be used as the solvent. Non-limiting examples of fluids that may be used include n-methyl-2-pyrrolidone, 2-pyrrolidone, propylene glycol, ethanol, and glycerin. The solvent may be a combination of any one or more of the above fluids and may optionally be combined with water, with normal saline, or with both water and normal saline. Other solvents that may be used individually or in combination with each other and/or with other solvents (including those recited above) include substances that are semi-solids or fluids at body temperature, which is about 37° C. for a human.

Non-limiting examples of substances that may used to form the lubricant formulation (lubricating substances), either with or without a solvent, include, but are not limited to, esters and ethers of cellulose, including, but not limited to, carboxymethylcellulose, hydroxy propyl methyl cellulose, methyl cellulose, and ethyl cellulose; sugars and carbohydrates, such as, but not limited to, maltodextrins, sorbitol, xylitol, maltose, glucose, sucrose, mannose, trehalose, corn syrup, and molasses; polymers and oligomers, such as, but not limited to, poly(vinyl pyrrolidone), polyethylene glycol, and polyethylene oxide; biopolymers and biomolecules such as, but not limited to, hyaluronic acid, collagen, polypeptides, poly-methylglutamate, gamma globulins, poly-benzyl-L-glutamate, albumin, chitosan, alginate, aliginic acid, fibrin, fibrin glue, fibrinogen, cellulosics, starches, dextran, dextrin, carageenan, heparin, glycosaminoglycans, polysaccharides, agrose, gelatin, and elastin; naturally occurring substances such but not limited to, mono-, di-, and triglycerides, cholesterol, and lecithin, and short, medium, long, and very long chain fatty acids and alcohols, both saturated and unsaturated; and oils and waxes such as, but not limited to, lauryl alcohol, myristyl alcohol, cetyl alcohol, stearyl alcohol, oleyl alcohol, lauric acid, myristic acid, palmitic acid, stearic acid, isostearic acid, and oleic acid; as well as other oils such as, but not limited to, mineral oil, petrolatum, cottonseed oil, coconut oil, sesame seed oil, peanut oil, isopropyl myristate and isopropyl palmitate. Some of these substances may fall into more than one category.

The lubricating substance may be a water soluble polymer. Non-limiting examples of water soluble polymers or oligomers include gelatin, albumin, dextrose, dextran, poly(ethylene glycol), poly(ethylene oxide), poly(vinylpyrrolidone), hydroxypropyl methyl cellulose, water soluble cellulose based polymers, hyaluronic acid, heparin, heparin sulfate, poly(vinyl alcohol), sialic acid, chitosan, gamma globulin, albumin, and combinations thereof. Other examples include, but are not limited to, homopolymers and copolymers (and homo-oligomers or co-oligomers) of acrylamide, acrylic acid, maleic acid, vinyl acetate, crotonic acid, vinylimidazole, maleic anhydride, and vinylpyrrolidone.

Any of the above lubricating substances may be used individually or in combination and may also be dissolved, dispersed, or both dissolved and dispersed in a solvent.

The lubricating substance in the lubricant formulation that may be dissolved, dispersed, or both dissolved and dispersed in the solvent may be present at about 1% to about 80%, preferably at about 2% to about 40%, and more preferably from about 5% to about 35% of the lubricant formulation where the % is a % by weight.

The lubricant formulation may also include a surfactant, either in addition to or instead of the lubricating substance.

Non-limiting examples of surfactants that may be used, either individually or in combination, include sorbitan oleate, sorbitan laurate, phospholipids, albumin, gelatin, lecithin, random and block copolymers of polyethylene oxide and polypropylene oxide, diblock and triblock copolymers of polyethylene oxide and polypropylene oxide such as PLURONIC® F68, PLURONIC® F127, and Poloxamer 407, polyvinyl alcohol, polysorbate 20, polysorbate 60, polysorbate 80, polyoxyethylene sorbitan oleates, polyoxyethylene sorbitan laurates, polyethylene glycol p-(1,1,3,3-tetramethyl-butyl)-phenyl ether (TRITON® X-100, Sigma-Aldrich), palmitate-co-polyethylene glycol, Vitamin E TGPS, ascorbyl palmitate, phosphatidylcholine, polyethylene glycol-phosphatidyl ethanolamine conjugate (PEG-PE), fatty acid esters (such as, without limitation, glycerol monostearate), sodium dodecyl sulfate (SDS), cellulose acetate, and quaternary ammonium compounds such as didodecyldimethyl ammonium bromide (DMAB). Vitamin E TPGS is also known as D-alpha tocopheryl polyethylene glycol 1000 succinate, and is a water soluble form of Vitamin E. A specification for Vitamin-E TPGS is listed in the United States National Formulary (NF). Polysorbates are a group of oleate esters of sorbitol and its' anhydrides condensed with polymers of ethylene oxide. Polysorbates are used as emulsifiers and surfactants in food, pharmaceuticals and cosmetics. Examples include polysorbate 20, polysorbate 60, and polysorbate 80, the specifications of which are all listed in the United States Pharmacopeia (USP). PLURONIC® is a trade name of BASF and encompasses a group of block copolymers formed from ethylene oxide and propylene oxide. Poloxamers are block copolymers with a central block of poly(propylene oxide) (PPO) and with a block of poly(ethylene oxide) (PEO) on each side where the PEO blocks are usually of the same length as determined by the number of constitutional units. Poloxamers type 407 is specified by a monograph in the National Formulary. Many of the PLURONIC® polymers are surfactants, and some of them also comply with one of the NF monographs for Poloxamers. Some of the above listed surfactants may also be biopolymers, water soluble polymers, lubricating substances, or a combination thereof.

The surfactant in the lubricant formulation may be present at about 0.05% to about 80%, preferably at about 0.1% to about 40%, and more preferably from about 0.2% to about 35% of the lubricant formulation where the % is a % by weight.

If a surfactant is present, the weight to weight ratio of the surfactant to the lubricating substance in the lubricant formulation may be from about 1:100 to about 10:1, from about 1:100 to about 1:1, from about 1:50 to about 10:1, from about 1:50 to about 1:1, from about 1:25 to about 5:1, from about 1:25 to about 2:1, from about 1:25 to about 1:1, from about 1:25 to about 1:5.

The lubricant formulation may include other non-toxic additives, such as, without limitation, antioxidants, stabilizers, colors, buffering agents, radio-opaque contrast agents, etc.

The lubricant formulation may have a viscosity, as determined at about 37° C., of 5 cP (centipoise) to 200,000 cP, and preferably 10 cP to 100,000 cP.

The lubricant formulation may be free of drugs, and in preferred embodiments, the lubricant formulation is free of drugs. The lubricant formulation may be free of all drugs save those substances that have a therapeutic effect in addition to performing another function, such as anti-oxidants, stabilizers, and buffers. Examples include vitamin E, such as Vitamin-E TPGS, which may be used as a solubilizer or surfactant, vitamin C, which may be used as a buffering agent, and calcium, salts of which may be used as diluents or fillers.

The lubricant formulation may consist of or consist essentially of a lubricating substance, a solvent, and other additives at a level of not more than 2% by weight and/or not more than 2% by volume of the lubricant formulation. The lubricant formulation may consist of or consist essentially of a lubricating substance and a solvent. The lubricant formulation may consist of or consist essentially of only one lubricating substance and a solvent. The lubricant formulation may consist of or consist essentially of a lubricating substance, a surfactant, and a solvent, where the lubricating substance and the surfactant are not the same substance. The lubricant formulation may consist of or consist essentially of a surfactant and a solvent. In any of the above embodiments, the lubricating substance may be selected from those listed above, the surfactant may be selected from those listed above, or a combination thereof. In any of the above embodiments, the solvent may be normal saline solution, and/or any of those listed herein. In any of the embodiments, the solvent may differ from the lubricating substance, the surfactant, or both.

The lubricating substances, surfactants, and other additives used in any of the lubricant formulations described herein are preferably biodegradable, of a sufficiently low molecular weight (not more than 40,000 Daltons) to pass through the kidneys, or both.

The lubricant formulation may be administered intra-arterially prior to, during, or both prior to and during the procedure in which the stent is delivered and deployed, that is during the stent implantation procedure. As used herein, "during the stent implantation procedure" means that the administration of the lubricant formulation occurs in the same operation as the stent implantation. The administration of the lubricant formulation may be a bolus administration, an infusion over a specific limited time period, or a combination thereof. The administration may be continuous or intermittent.

The lubricant formulation may be administered, or the administration may begin, within 30 to 90 minutes, within 5 to 75 minutes, within 10 to 45 minutes, within 5 to 30 minutes, within 2 to 20 minutes, or within 15 minutes prior to the insertion of the stent delivery device, typically a catheter, that will deliver the stent into the patient. The lubricant formulation may be administered, or administration may begin, during the time that the stent delivery device is in the patient, but before the deployment of the stent, during the deployment of the stent, or both before and during the deployment of the stent. The lubricant formulation may be administered at the vascular region within minutes, for example within 10 minutes, within 5 minutes, or within 2 minutes, of the deployment of the stent at the vascular region. The administration of the lubricant formulation at the site of the implantation may begin within minutes, for example within 10 minutes, within 5 minutes, or within 2 minutes, of the deployment of the stent at the vascular region, and may overlap, at least in part, the time of stent deployment.

In some embodiments, the lubricant formulation may be administered intra-arterially. Non-limiting devices that may be used for the intra-arterial administration of the drug include a catheter, a catheter with holes, a dual balloon, and balloons and balloon catheters of various designs.

Figure 4:
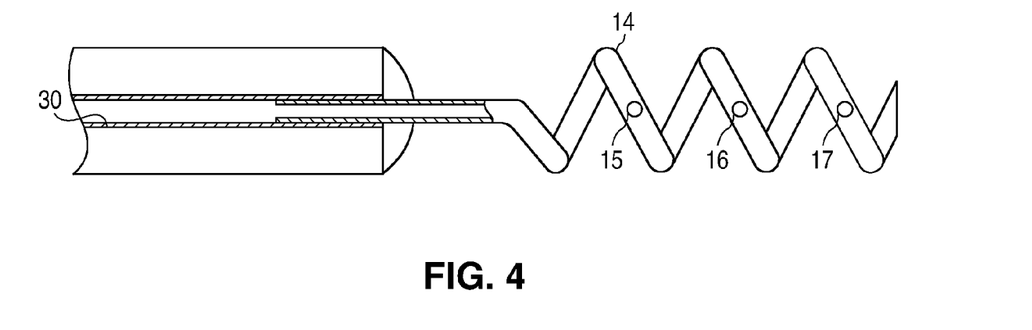
FIG. 4 is a schematic depiction of a catheter tip with a closed end, and holes on the side for fluid delivery.

As described previously, a lumen in the shaft of a catheter may be used to deliver fluids to a vascular region. In other embodiments, a catheter specifically designed to administer fluids, such as an infusion catheter, may be used to administer the lubricant formulation to the vascular region prior to the deployment of the stent. In still other embodiments, a catheter may have multiple lumens, such as one for inflating a balloon, and a second for delivery of a fluid or other substance. Thus, the lubricant formulation may be administered by the same catheter used for delivery and deployment of the stent. The lubricant formulation may be administered by a catheter in which the lumen used for fluid delivery is designed to have a closed tip, but a series of holes along the sides. An example of such a catheter tip is illustrated in FIG. 4 where helical tip 14 is connected to the tube 30 within the catheter and catheter tip 14 has holes 15, 16, and 17 that allow for fluid flow.

The lubricant formulation may be disposed over at least a portion of, part of, substantially all of, or the entire outer surface of the balloon of a balloon catheter thus forming a coating on the balloon. Thus, administration may occur by disposing the lubricant formulation over part of, substantially all of, all of the outer surface, or the working surface of a balloon prior to the dilation of the vessel and implantation of the stent. The balloon catheter may be delivered to the site, and the balloon may then be inflated, transferring the lubricant formulation to the vessel wall. In some embodiments, the lubricant formulation may be disposed over the entire outer surface, the entire length, the entire working length, or substantially the entire working length or working area (described below) of the balloon, including the stented section, and the lubricant formulation may include, but is not limited to, or may consist essentially of a water soluble polymer or oligomer. In such embodiments, the lubricant formulation may be disposed over at least a portion of the outer surface of the stent that is exposed when the stent is crimped onto the balloon.

Figure 5:
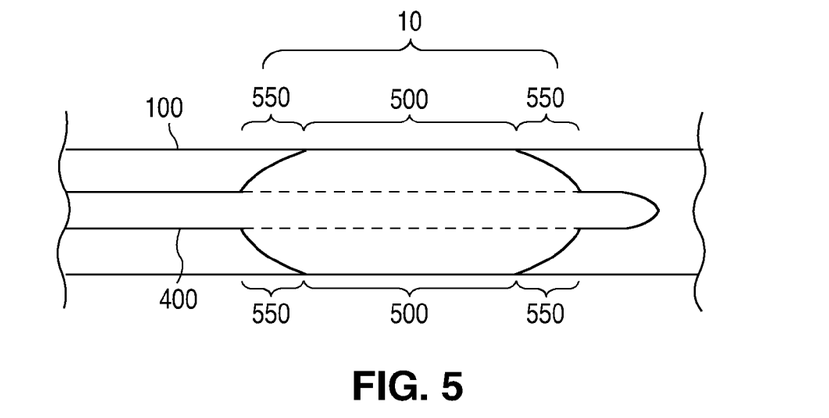
FIG. 5 is a schematic depiction of a typical balloon of a catheter balloon having substantially one diameter when inflated.
Figure 6:
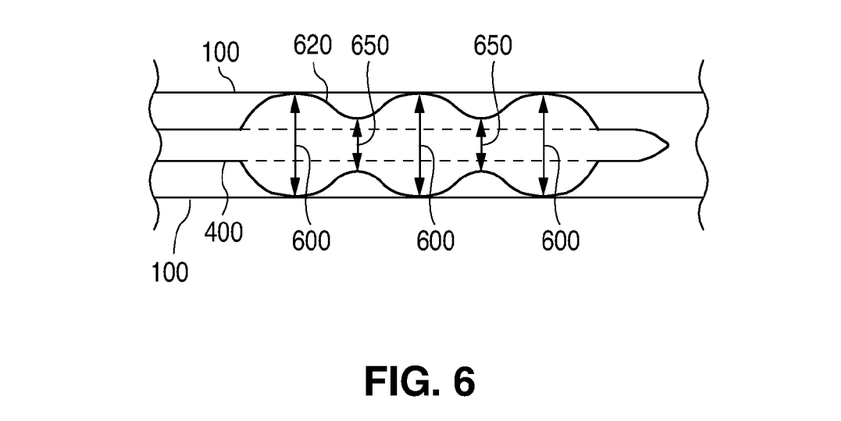
FIG. 6 is a schematic depiction of a non-limiting example of a balloon catheter which has a balloon with multiple diameters that when inflated, a work zone is created between the larger and smaller diameters.
Figure 7:
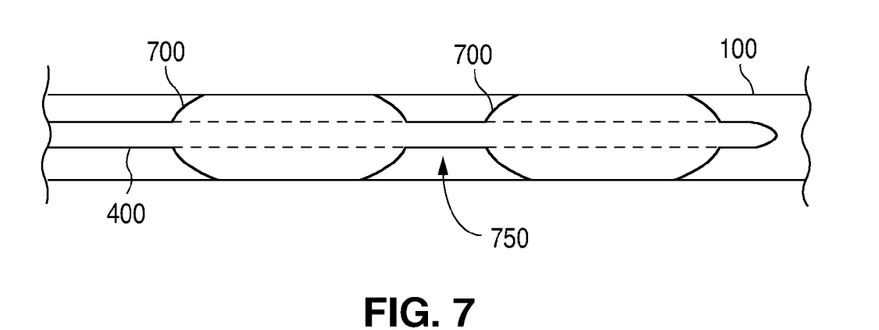
FIG. 7 is a schematic depiction of a non-limiting example of a dual balloon catheter which has two balloons such that when the dual balloons are inflated, a work zone is created between the dual balloons.

In addition to the balloon described previously, a balloon which comprises two different outside diameters may be used for the delivery. A "typical" balloon has substantially a single diameter over its entire length such that the full length of the balloon is in contact with the luminal surface of the vessel, as shown in FIG. 5. FIG. 5 also shows what is meant by "substantially" a single diameter. As can be seen in the FIG. 5, the ends 550 of balloon 520 are not necessarily square so that the balloon curves down to join the catheter tube but the major portion of balloon length 500, which comprises the interface in contact with the lumen 10, has substantially the same diameter. For a balloon having substantially a single diameter over its entire length, the interface in contact with the lumen, 10, may also be referred to as the "working length" or "working area." In contrast, an example of a balloon with two different outside diameters is depicted in FIG. 6 wherein balloon 620 attached to catheter 400 has first diameters 600, which contact vessel wall 100 and second diameters 650 which do not contact with vessel wall 100. More generically, at each end of the balloon is a first diameter, which is the same as the diameter of the single diameter balloon described above and which contacts the luminal surface of the vessel, and between the end first diameters may be any number of additional first diameters. Each such first diameter is separated from each other such diameter by a second diameter which is less than the inside diameter of the vessel and therefore does not contact the luminal surface. Of course, use of the term "a second diameter" is nominal; the point is that there are regions between the first diameters that are not in contact with the luminal surface and the diameters of those regions may be identical or all may be different; for the purposes of this discussion it is assumed that they are all the same. Another type of balloon catheter is shown in FIG. 7. The balloon catheter depicted in FIG. 7 has two (or more) balloons 700 mounted on a catheter 400 such that when the two (or more) balloons 700 are inflated and in contact vessel wall 100, a work zone(s) 750 is created between the two (or more) balloons.

In some embodiments, the lubricant formulation may be released from the middle section of a dual balloon catheter or a catheter balloon having "substantially" two diameters where the middle section is the section of the balloon that is not in contact with the lumen wall between the first diameters at the ends of the balloon that do contact the lumen wall when inflated. In some embodiments, the stent may be mounted on the balloon, and the stent may be deployed following the inflation of the balloon and release of the lubricant formulation. In some embodiments, the stent may be mounted on the middle section.

A balloon used to administer lubricant formulation in the methods of this invention may be microporous. A microporous balloon comprises a thin membrane in which a large number of holes, which may be of substantially uniform size, have been created. The holes can range in size from tens of nanometers to microns and can be created by a number of techniques including, but not limited to, laser drilling. Alternatively, the holes or pores may be created by ab initio synthesis. In the latter case, the membrane is synthesized in such a manner that voids, openings, or channels are left in the structure formed. A microporous balloon formed by these or any other procedure may be used.

When using a microporous balloon, the lubricant formulation may be used as the fluid to expand the balloon, or may be combined with the fluid used to expand the balloon. When the balloon is expanded, rather than simply leaking out of the balloon in an uncontrolled manner, the size of the holes may result in a slow, controlled "weeping" of fluid, in this case the lubricant formulation, from the holes. In some embodiments, if a balloon having two diameters as discussed above is used, only those portions of the balloon having the first diameter, that is, the portions that are in contact with the luminal surface may be microporous with the regions characterized by the second diameter are non-porous. In alternative embodiments, one or more of the regions of the balloon having the second diameter may be microporous either in addition to or instead of those portions have the first diameter. In this case, the lubricant formulation will be administered into the arterial lumen instead of, or in addition to, directly onto the luminal surface. In another embodiment, the lubricant formulation may be administered by catheter or by another method to the working area of a dual balloon.

In some embodiments, the lubricant formulation is administered proximal to the vascular region to be treated or at the vascular region to be treated (stented segment once stented) using a specially designed catheter or medical device that allows for occlusion of the vessel, such as a blood vessel, and then administration of the lubricant formulation during the time period of occlusion. After a limited duration of time, the administration of the lubricant formulation is stopped and the occlusion is removed allowing the lumen to open again. This process is performed repeatedly or cycled. The occlusion in each cycle is limited in duration but the total duration of occlusion may be increased by performing several cycles.

In any of the embodiments, the lubricant formulation may be administered proximal to the vascular region to be treated, or at the vascular region.

In some embodiments, the methods of treating, preventing, or ameliorating a vascular disease and/or disorder in a diabetic or pre-diabetic patient who is in need of treating, preventing, or ameliorating a vascular disease and/or disorder, and who may be identified as having a diabetic condition or a pre-diabetic condition also comprises, in addition to the administration of a lubricant formulation and implantation of a stent, the use of, that is delivery and deployment of, a drug coated balloon. A drug coated balloon (DCB) is a balloon of a balloon catheter that has a coating of a drug or a coating containing a drug disposed over at least a portion of the outer surface of the balloon. When the balloon is inflated, and the balloon walls contact the vessel walls, the drug is released. The underlying structure of the balloon can be virtually any structural design and the balloon can be composed of any suitable material. A drug coating disposed over all or a portion of the outer surface of the balloon may include only a drug, or the coating may include a drug in combination with another material such as a polymer.

The drug of the DCB is not limited. In preferred embodiments, the drug of the DCB may be an anti-inflammatory, either steroidal or non-steroidal, an antiproliferative, a thiazolidinedione, or a combination thereof.

A DCB may be expanded prior to administration of the lubricant formulation and deployment of the stent, after the administration of the lubricant formulation, but prior to the deployment of the stent, or both after the administration of the lubricant formulation and the deployment of the stent. A DCB may be used to deploy the stent, and may have a lubricant formulation disposed over at least a portion of the outer surface of the DCB, and optionally, the stent, if mounted on the DCB. The DCB may be expanded within (before or after) 4 hours of the deployment of the stent, preferably within 2 hours, and more preferably within 1 hour. In preferred embodiments, the DCB may be deployed prior to the deployment of the stent and the initiation of any lubricant administration.

In some embodiments of the present invention, the stent implanted may be a stent without any drug, such as, but not limited to, a BMS or a stent of another material or another material in combination with a metal, while in other embodiments the stent may be a DES. The stent may be of any design. The stent may be a self-expanding stent, or a balloon expandable stent. The stent may be formed from a polymer, a metal, a metal alloy, a ceramic, a glass, and any combination thereof. The stent may be made from biostable materials, biodegradable materials, or any combination of biostable and biodegradable materials.

If the stent is a DES, the stent may be any type of DES. Examples include, without limitation, stents with holes, grooves, pores, indentations, or a combination thereof in the surface where at least a portion of the drug may be contained within at least a portion of the holes, grooves, pores, indentations or combinations thereof porous or hollow stents where at least a portion of the drug may be contained within the pores or within the hollow interior of the stent; and stents with at least a portion of the drug contained in a coating disposed over at least a portion of the outer surface of the stent. The coating disposed over the or a portion of the outer surface may include only a drug, or may include a drug in combination with another material, such as, but not limited to, a polymer, a metal, a metal alloy, a ceramic, a glass, or a combination thereof. A stent used in the methods of the invention may include any logical combination of the above features.

The stent may be a bioabsorbable stent having at least a portion of the drug may be included in the device body of the stent. As a non-limiting example, the stent may be a bioabsorbable polymeric stent with at least a portion of the drug being dispersed within the polymeric device body of the stent.

Porous and hollow stents, stents with grooves, holes, indentations, pores or a combination thereof, and bioabsorbable stents may have a coating disposed over at least a portion of the outer surface of the stent. The stent coating may or may not include the drug. The stent coating, if present, may be formed from a polymer, a metal, a metal alloy, a ceramic, a glass, or a combination thereof. Stent coatings may be constructed of multiple layers; the coating may be applied as multiple layers; or both. Multiple layers may have different materials, different ratios of materials, or both in each layer. A coating that is disposed over at least a portion of the outer surface of the stent may have a thickness of less than or about equal to 30 microns, less than or about equal to 20 micron, less than or about equal to 10 micron, less than or about equal to 5 micron, or less than or about equal to 3 micron. These dimensions may apply to an individual layer if more than one layer is disposed over the outer surface of the stent, to the total of all layers, or to both an individual layer and to the total of all layers. If a stent coating with drug has multiple layers, the drug may be included in only one layer, more than on layer but not all layers, or all layers.

A bioabsorbable stent may have a coating containing a drug disposed over at least a portion of the outer surface instead of or in addition to having drug incorporated into the device body of the bioabsorbable stent, and the drug of the coating may be the same as or different from the drug of the device body. In general, the stent may include any consistent combination of the above features, and where a drug is incorporated in more than one manner, the drugs incorporated in different manners may be the same or different. For example, the stent may be a bioabsorbable porous stent, where the pores may include a drug, the device body of the stent may include a drug, or the pores and the device body may include a drug, and if both, the drugs may be the same or different, and the stent may also have a coating, which may or may not include a drug, and if a drug is included, the drug may be the same or different from the drug of the pores and the drug of the device body of the stent.

If a DES is used and/or a DCB is used, the drug of either the DES or the DCB may independently be, but is not limited to, rapamycin (sirolimus), Biolimus A9, myolimus, deforolimus, AP23572 (Ariad Pharmaceuticals), tacrolimus, temsirolimus, pimecrolimus, novolimus, zotarolimus (ABT-578), 40-O-(2-hydroxy)ethyl-rapamycin (everolimus), 40-O-(3-hydroxypropyl)rapamycin, 40-O-[2-(2-hydroxy)ethoxy]ethyl-rapamycin, 40-O-tetrazolylrapamycin, or 40-epi-(N1-tetrazolyl)-rapamycin. The above drugs may be used in combination with each other and/or with other drugs.

Polymers that may be used to prepare coatings disposed over at least a portion of the outer surface of a stent, the device body of a stent, a material from which the device body of a stent is formed, or a part of a stent include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoesters, polyanhydrides, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amides, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, rayon, rayon-triacetate, cellophane, and cellulose derivatives, including, but not limited to, cellulose acetate, cellulose butyrate, cellulose acetate butyrate, cellulose nitrate, cellulose propionate, cellulose ethers, and carboxymethyl cellulose. Additional representative examples of polymers include ethylene vinyl alcohol copolymer (commonly known by the generic name EVOH or by the trade name EVAL®), poly (butyl methacrylate), poly(vinylidene fluoride-co-hexafluoropropene) (e.g., SOLEF® 21508, available from Solvay Solexis PVDF, Thorofare, N.J.), polyvinylidene fluoride (otherwise known as KYNAR®, available from Atofina Chemicals, Philadelphia, Pa.), ethylene-vinyl acetate copolymers, poly(vinyl acetate), styrene-isobutylene-styrene triblock copolymers, and polyethylene glycol. Polymers may be used individually, or in any combination of two or more polymers in any proportion. A polymers may also be used in combination with another materials, such as, but not limited to, a metal, a metal alloy, a glass, a ceramic, and a combination thereof.

As used herein, "lactide" encompasses L-lactide, D, L-lactide, D-lactide, meso-lactide, and any combination thereof, unless a type is specifically recited.

As used herein, the terms poly(D,L-lactide), poly(L-lactide), poly(D,L-lactide-co-glycolide), and poly(L-lactide-co-glycolide) are used interchangeably with the terms poly(D, L-lactic acid), poly(L-lactic acid), poly(D,L-lactic acid-co-glycolic acid), and poly(L-lactic acid-co-glycolic acid), respectively.

Various non-limiting embodiments of the present invention are described in the following numbered paragraphs, paragraphs (1) to (35):

(1) A method of treating, preventing, or ameliorating a vascular disease and/or disorder in a diabetic patient or a pre-diabetic patent, the method including, but not limited to, delivering a stent to a vascular region of a patient, and deploying the stent at the vascular region of the patient; and, prior to, during, or both prior to and during the deployment of the stent, administering (delivering) a lubricant formulation proximally to, at, or both proximally to and at the vascular region of the patient; wherein the patient is in need of treating, preventing, or ameliorating a vascular disease and/or disorder.

(2) The method as described in paragraph (1), wherein lubricant formulation administration includes, but is not limited to, release from a catheter, the catheter being used to deliver the lubricant formulation.

(3) The method as described in paragraph (1) or (2), wherein the lubricant formulation administration includes, but is not limited to, delivery through an array of holes in a catheter.

(4) The method as described in paragraph (1) or (2), wherein the catheter is used to deliver and deploy the stent.

(5) The method as described in paragraph (4), wherein the release of the lubricant formulation from the catheter occurs when the stent is ready to deploy but before the stent is actually deployed.

(6) The method as described in paragraph (4) or (5), wherein the release of the lubricant formulation from the catheter occurs during the deployment of the stent.

(7) The method as described in any one of paragraphs (1)-(6), wherein the lubricant formulation administration includes, but is not limited to, delivery from a balloon used prior to dilatation of the vascular region and wherein the delivery of the stent includes, but is not limited to, delivery by a stent delivery system which does not include the pre-dilation balloon.

(8) The method as described in any one of paragraphs (1)-(3), wherein the lubricant formulation administration includes, but is not limited to, release from the middle section of a dual balloon, and wherein the stent is also mounted on the balloon and is deployed simultaneously with the balloon inflation and lubricant formulation release.

(9) The method as described in any one of paragraphs (1)-(3), wherein the lubricant formulation administration includes, but is not limited to, release from the middle section of a balloon having more than substantially one diameter, and wherein the stent is also mounted on the balloon and is deployed simultaneously with the balloon inflation and lubricant formulation release.

(10) The method as described in any one of paragraphs (1)-(3), wherein the lubricant formulation administration includes, but is not limited to, delivery from a catheter balloon, the stent being mounted on at least a portion of the length of the catheter balloon, and the lubricant formulation being disposed over the entire length, or substantially the entire length, of the balloon.

(11) The method as described in paragraph (10), wherein the lubricant formulation is also disposed over at least a portion of the mounted stent.

(12) The method as described in any one of paragraphs (1)-(11), wherein the lubricant formulation includes, but is not limited to, a solvent.

(13) The method as described in paragraph (12), wherein the solvent includes, but is not limited to, a substance selected from the group consisting of water, a normal saline solution, n-methyl-2-pyrrolidone, 2-pyrrolidone, propylene glycol, ethanol, glycerin, and combinations thereof.

(14) The method as described in paragraph (12) or (13), wherein the solvent includes, but is not limited to, a substance that is a semi-solid or liquid at about 37° C.

(15) The method as described in any one of paragraphs (1)-(14), wherein the lubricant formulation includes, but is not limited to, a substance selected from the group consisting of carboxymethyl-cellulose, hyaluronic acid, polyvinylpyrolidone, polyethylene glycol, polyethylene oxide, and heparin.

(16) The method as described in any one of paragraphs (1)-(15), wherein the lubricant formulation includes, but is not limited to, a surfactant.

(17) The method as described in paragraph (16), wherein the surfactant is selected from the group consisting of diblock copolymers and co-oligomers of polyethylene oxide-co-polypropylene oxide, triblock copolymers of polyethylene oxide-co-polypropylene oxide, polyvinyl alcohol, polysorbate 20, polysorbate 60, polysorbate 80, and polyethylene glycol p-(1,1,3,3-tetramethylbutyl)-phenyl ether (Triton X-100), palmitate-co-polyethylene glycol, and combinations thereof.

(18) The method as described in any one of paragraphs (1)-(17), wherein the lubricant formulation includes, but is not limited to, a water miscible polymer, a water soluble oligomer, a biopolymer, a biomolecule, or a combination thereof.

(19) The method as described in any one of paragraphs (1)-(11), wherein the lubricant formulation consists essentially of a water miscible polymer, a water soluble oligomer, a biopolymer, a biomolecule, or a combination thereof.

(20) The method as described in paragraph (18) or (19), wherein the water miscible polymer, the water soluble oligomer, the biopolymer, the biomolecule, or the combination thereof is selected from the group consisting of gelatin; albumin; dextrose; dextran; poly(ethylene glycol); poly(ethylene oxide); poly(vinylpyrrolidone); hydroxypropyl methyl cellulose; water soluble cellulose based polymers; hyaluronic acid; heparin; heparin sulfate; poly(vinyl alcohol); sialic acid; chitosan; gamma globulin; albumin; homopolymers and copolymers (and homo-oligomers and co-oligomers) of acrylamide, acrylic acid, maleic acid, vinyl acetate, crotonic acid, vinylimidazole, maleic anhydride, and vinylpyrrolidone; and combinations thereof.

(21) The method as described in any one of paragraphs (1)-(20), wherein the lubricant formulation is administered or the administration begins within 30 to 90 minutes prior to the insertion of the stent delivery device.

(22) The method as described in any one of paragraphs (1)-(20), wherein the lubricant formulation is administered or the administration begins within 5 to 75 minutes prior to the insertion of the stent delivery device.

(23) The method as described in any one of paragraphs (1)-(20), wherein the lubricant formulation is administered or the administration begins within 10 to 45 minutes prior to the insertion of the stent delivery device.

(24) The method as described in any one of paragraphs (1)-(20), wherein the lubricant formulation is administered or the administration begins within 5 to 30 minutes prior to the insertion of the stent delivery device.

(25) The method as described in any one of paragraphs (1)-(20), wherein the lubricant formulation is administered or the administration begins within 2 to 20 minutes prior to the insertion of the stent delivery device.

(26) The method as described in any one of paragraphs (1)-(20), wherein the lubricant formulation is administered or the administration begins within 15 minutes prior to the insertion of the stent delivery device.

(27) The method as described in any one of paragraphs (1)-(26), wherein the lubricant formulation is administered during the time that the stent delivery device is in the patient, but prior to deployment of the stent.

(28) The method as described in any one of paragraphs (1)-(27), wherein the lubricant formulation is administered during the deployment of the stent.

(29) The method as described in any one of paragraphs (1)-(28), wherein the lubricant formulation is administered within 10 minutes of the deployment of the stent at the vascular region.

(30) The method as described in paragraph (29), wherein the lubricant formulation is administered within 5 minutes of the deployment of the stent at the vascular region.

(31) The method as described in paragraph (30), wherein the lubricant formulation is administered within 2 minutes of the deployment of the stent at the vascular region.

(32) The method as described in any one of paragraphs (1)-(24), wherein the method further includes, but is not limited to, the use of a DCB.

(33) The method as described in paragraph (32), wherein the DCB is delivered and deployed prior to the initiation of delivery of the lubricant formulation and prior to the deployment of the stent.

(34) The method as described in any one of paragraphs (1)-(33), wherein the administration of the lubricant formulation includes, but is not limited to, administration of the lubricant formulation during at least one time period in which the vessel with vascular region to be treated is occluded and wherein the vessel with the vascular region to be treated is occluded one or more times.

(35) The method as described in any one of paragraphs (1)-(34), wherein the patient is identified as having a diabetic condition or a pre-diabetic condition.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can logically be incorporated without undue experimentation.

What is claimed is:

1. A method of treating, preventing, or ameliorating a vascular disease, a vascular disorder, or both, in a diabetic or pre-diabetic patient, the method comprising:
    delivering a stent to, and deploying the stent at a vascular region of a patient; and
    prior to, during, or both prior to and during the deployment of the stent, administering a lubricant formulation to the vascular region of the patient;
    wherein the patient is identified as having a diabetic condition or a pre-diabetic condition;
    wherein the patient is in need of treating, preventing, or ameliorating a vascular disease, a vascular disorder, or both;
    wherein the lubricant formulation administration comprises delivery by a balloon, a dual balloon, a balloon catheter, a guide catheter, a micro-catheter, or a combination thereof;
    wherein
        the lubricant formulation comprises at least one solvent selected from the group consisting of 2-pyrrolidone, and glycerin;
        or
        the lubricant formulation comprises at least one substance selected from the group consisting of carboxymethyl-cellulose, hydroxy propyl methyl cellulose, methyl cellulose, ethyl cellulose, cellulose acetate, sorbitol, xylitol, corn syrup, molasses, fibrin, fibrin glue, fibrinogen, cellulosics, poly-methyl-glutamate, gamma globulins, poly-benzyl-L-glutamate, albumin, chitosan, alginate, aliginic acid, dextrin, carageenan, agrose, gelatin, elastin, lauric acid, myristic acid, palmitic acid, stearic acid, isostearic acid, mineral oil, petrolatum, cottonseed oil, coconut oil, sesame seed oil, peanut oil, isopropyl palmitate, poly(vinyl alcohol), sialic acid, homopolymers and copolymers (and homo-oligomers and co-oligomers) of acrylamide, homopolymers and copolymers (and homo-oligomers and co-oligomers) of maleic acid, homopolymers and copolymers (and homo-oligomers and co-oligomers) of vinyl acetate, homopolymers and copolymers (and homo-oligomers and co-oligomers) of crotonic acid, homopolymers and copolymers (and homo-oligomers and co-oligomers) of vinylimidazole, homopolymers and copolymers (and homo-oligomers and co-oligomers) of maleic anhydride, polyethylene glycol p-(1,1,3,3-tetramethylbutyl)-phenyl ether, palmitate-co-polyethylene glycol, ascorbyl palmitate, and polyethylene glycol-phosphatidyl ethanolamine conjugate;

or wherein the lubricant formulation comprises at least one solvent selected from the group consisting of 2-pyrrolidone, and glycerin; and the lubricant formulation comprises at least one substance selected from the group consisting of carboxymethyl-cellulose, hydroxy propyl methyl cellulose, methyl cellulose, ethyl cellulose, cellulose acetate, sorbitol, xylitol, corn syrup, molasses, collagen, fibrin, fibrin glue, fibrinogen, cellulosics, poly-methylglutamate, gamma globulins, poly-benzyl-L-glutamate, albumin, chitosan, alginate, aliginic acid, dextrin, carageenan, agrose, gelatin, elastin, lecithin, lauric acid, myristic acid, palmitic acid, stearic acid, isostearic acid, mineral oil, petrolatum, cottonseed oil, coconut oil, sesame seed oil, peanut oil, isopropyl palmitate, poly(vinyl alcohol), sialic acid, homopolymers and copolymers (and homo-oligomers and co-oligomers) of acrylamide, homopolymers and copolymers (and homo-oligomers and co-oligomers) of maleic acid, homopolymers and copolymers (and homo-oligomers and co-oligomers) of vinyl acetate, homopolymers and copolymers (and homo-oligomers and co-oligomers) of crotonic acid, homopolymers and copolymers (and homo-oligomers and co-oligomers) of vinylimidazole, homopolymers and copolymers (and homo-oligomers and co-oligomers) of maleic anhydride, polyethylene glycol p-(1,1,3,3-tetramethylbutyl)-phenyl ether, palmitate-co-polyethylene glycol, ascorbyl palmitate, and polyethylene glycol-phosphatidyl ethanolamine conjugate;

and wherein the lubricant formulation is a fluid that is free of drugs, wherein said drugs do not include said solvents and said substances of the lubricant formulation.

2. The method of claim 1, wherein the lubricant formulation administration comprises delivery by a catheter, the catheter having an array of holes through which the formulation is administered, and the catheter being used to deliver the lubricant formulation and optionally used to deliver and deploy the stent.

3. The method of claim 1, wherein the lubricant formulation administration comprises release from a dual balloon, the dual balloon comprising two balloons on a catheter shaft each of which contact the lumen wall, and a middle section that does not contact the lumen wall between the two balloons, the lubricant being released from the middle section.

4. The method of claim 1, wherein the lubricant formulation administration comprises delivery from a balloon used prior to dilatation of the vascular region and wherein the delivery of the stent comprises delivery by a stent delivery system which does not comprise the pre-dilatation balloon.

5. The method of claim 1, wherein the lubricant formulation administration comprises release from a catheter, the catheter being used to deliver the lubricant formulation and optionally used to deliver and deploy the stent.

6. The method of claim 5, wherein the release of the lubricant formulation from the catheter occurs when the stent is ready to deploy but before the stent is actually deployed.

7. The method of claim 5, wherein the release of the lubricant formulation from the catheter occurs when the stent is ready to deploy, during the deployment of the stent, or both when the stent is ready to deploy and during the deployment of the stent.

8. The method of claim 1, wherein the lubricant formulation comprises at least one substance selected from the group consisting of alginate, aliginic acid, dextrin, poly(vinyl alcohol), chitosan, and carageenan.

9. The method of claim 1, wherein the lubricant formulation comprises at least one substance selected from the group consisting of corn syrup, and molasses.

10. The method of claim 1, wherein the lubricant formulation comprises at least one substance selected from the group consisting of homopolymers and copolymers (and homo-oligomers and co-oligomers) of maleic acid, homopolymers and copolymers (and homo-oligomers and co-oligomers) of crotonic acid, homopolymers and copolymers (and homo-oligomers and co-oligomers) of vinylimidazole, and homopolymers and copolymers (and homo-oligomers and co-oligomers) of maleic anhydride.

11. The method of claim 1, the method further comprising the delivery of a drug coated balloon to the vascular region and expansion of the drug coated balloon to release the drug of the drug coated balloon at the vascular region.

12. The method of claim 1, wherein the administration of the lubricant formulation occurs prior to, or both prior to and during the deployment of the stent.

13. The method of claim 1, wherein the administration of the lubricant formulation occurs prior to the deployment of the stent.

14. The method of claim 1, wherein the lubricant formulation comprises at least one substance selected from the group consisting of carboxymethyl-cellulose, hydroxy propyl methyl cellulose, methyl cellulose, ethyl cellulose, cellulose acetate, fibrin, fibrin glue, fibrinogen, cellulosics, and isopropyl palmitate.

15. The method of claim 1, wherein the lubricant formulation comprises at least one substance selected from the group consisting of palmitate-co-polyethylene glycol, isopropyl palmitate, ascorbyl palmitate, phosphatidylcholine, and polyethylene glycol-phosphatidyl ethanolamine conjugate.

16. The method of claim 1, wherein the lubricant formulation comprises at least one substance selected from the group consisting of sialic acid, lauric acid, myristic acid, palmitic acid, stearic acid, and isostearic acid.

17. The method of claim 1, wherein the lubricant formulation comprises at least one substance selected from the group consisting of mineral oil, cottonseed oil, coconut oil, sesame seed oil, and peanut oil.

18. The method of claim 1, wherein the lubricant formulation comprises at least one substance selected from the group consisting of poly-methylglutamate, gamma globulins, poly-benzyl-L-glutamate, and albumin.

19. The method of claim 1, wherein the lubricant formulation consists of one or more solvents, one or more substances, and optionally, one or more surfactants;

wherein the solvent(s) are independently selected from the group consisting of n-methyl-2-pyrrolidone, 2-pyrrolidone, propylene glycol, ethanol, glycerin, water, and normal saline;

wherein the substance(s) are independently selected from the group consisting of carboxymethylcellulose, hydroxy propyl methyl cellulose, methyl cellulose, ethyl cellulose, maltodextrins, sorbitol, xylitol, maltose, glucose, sucrose, mannose, trehalose, corn syrup, molasses, poly(vinyl pyrrolidone), polyethylene glycol, polyethylene oxide, hyaluronic acid, collagen, polypeptides, poly-methylglutamate, gamma globulins, poly-benzyl-L-glutamate, albumin, chitosan, alginate, aliginic acid, fibrin, fibrin glue, fibrinogen, starches, dextran, dextrin, carageenan, heparin, glycosaminoglycans, polysaccharides, agrose, gelatin, elastin, mono-, di-, and triglycerides, cholesterol, lecithin, short, medium, long, and very long chain saturated and unsaturated fatty acids and alcohols, lauryl alcohol, myristyl alcohol, cetyl alcohol, stearyl alcohol, oleyl alcohol, lauric acid, myristic acid, palmitic acid, stearic acid, isostearic acid, oleic acid, mineral oil, petrolatum, cottonseed oil, coconut oil, sesame seed oil, peanut oil, isopropyl myristate, isopropyl palmitate, gelatin, albumin, dextrose, poly(ethylene glycol), poly(ethylene oxide), poly(vinylpyrrolidone), hydroxypropyl methyl cellulose, water soluble cellulose based polymers, hyaluronic acid, heparin, heparin sulfate, poly(vinyl alcohol), sialic acid, chitosan, gamma globulin, albumin, homopolymers and copolymers (and homo-oligomers and co-oligomers) of acrylamide, homopolymers and copolymers (and homo-oligomers and co-oligomers) of acrylic acid, homopolymers and copolymers (and homo-oligomers and co-oligomers) of maleic acid, homopolymers and copolymers (and homo-oligomers and co-oligomers) of vinyl acetate, homopolymers and copolymers (and homo-oligomers and co-oligomers) of crotonic acid, vinylimidazole, homopolymers and copolymers (and homo-oligomers and co-oligomers) of maleic anhydride, and homopolymers and copolymers (and homo-oligomers and co-oligomers) of vinylpyrrolidone;

wherein the surfactant(s) are independently selected from the group consisting of sorbitan oleate, sorbitan laurate, phospholipids, albumin, gelatin, lecithin, random and block copolymers of polyethylene oxide and polypropylene oxide, diblock copolymers and co-oligomers of polyethylene oxide and polypropylene oxide, triblock copolymers of polyethylene oxide and polypropylene oxide, Poloxamer 407, polyvinyl alcohol, polysorbate 20, polysorbate 60, polysorbate 80, polyoxyethylene sorbitan oleates, polyoxyethylene sorbitan laurates, polyethylene glycol p-(1,1,3,3-tetramethylbutyl)-phenyl ether, palmitate-co-polyethylene glycol, Vitamin E TGPS, ascorbyl palmitate, phosphatidylcholine, polyethylene glycol-phosphatidyl ethanolamine conjugate (PEG-PE), fatty acid esters, glycerol monostearate, sodium dodecyl sulfate (SDS), cellulose acetate, and didodecyldimethyl ammonium bromide (DMAB).

20. A method of treating, preventing, or ameliorating a vascular disease, a vascular disorder, or both, in a diabetic or pre-diabetic patient, the method comprising:
  delivering a stent to, and deploying the stent at a vascular region of a patient; and
  prior to, during, or both prior to and during the deployment of the stent, administering a lubricant formulation to the vascular region of the patient;
  wherein the patient is identified as having a diabetic condition or a pre-diabetic condition;
  wherein the patient is in need of treating, preventing, or ameliorating a vascular disease, a vascular disorder, or both;
  wherein the lubricant formulation administration comprises delivery by a balloon, a dual balloon, a balloon catheter, a guide catheter, a micro-catheter, or a combination thereof;
  wherein
    the lubricant formulation comprises at least one solvent selected from the group consisting of 2-pyrrolidone, and glycerin;
    or
    the lubricant formulation comprises at least one substance selected from the group consisting of lauryl alcohol, myristyl alcohol, cetyl alcohol, stearyl alcohol, and oleyl alcohol;
    or
    the lubricant formulation comprises at least one solvent selected from the group consisting of 2-pyrrolidone, and glycerin; and the lubricant formulation comprises at least one substance selected from the group consisting of lauryl alcohol, myristyl alcohol, cetyl alcohol, stearyl alcohol, and oleyl alcohol;
  and
  wherein the lubricant formulation is a fluid that is free of drugs, wherein said drugs do not include said solvents and said substances of the lubricant formulation.

21. The method of claim 20, wherein
the lubricant formulation consists of one or more solvents, one or more substances, and optionally, one or more surfactants;
wherein the solvent(s) are independently selected from the group consisting of n-methyl-2-pyrrolidone, 2-pyrrolidone, propylene glycol, ethanol, glycerin, water, and normal saline;
wherein the substance(s) are independently selected from the group consisting of carboxymethylcellulose, hydroxy propyl methyl cellulose, methyl cellulose, ethyl cellulose, maltodextrins, sorbitol, xylitol, maltose, glucose, sucrose, mannose, trehalose, corn syrup, molasses, poly(vinyl pyrrolidone), polyethylene glycol, polyethylene oxide, hyaluronic acid, collagen, polypeptides, poly-methylglutamate, gamma globulins, poly-benzyl-L-glutamate, albumin, chitosan, alginate, aliginic acid, fibrin, fibrin glue, fibrinogen, starches, dextran, dextrin, carageenan, heparin, glycosaminoglycans, polysaccharides, agrose, gelatin, elastin, mono-, di-, and triglycerides, cholesterol, lecithin, short, medium, long, and very long chain saturated and unsaturated fatty acids and alcohols, lauryl alcohol, myristyl alcohol, cetyl alcohol, stearyl alcohol, oleyl alcohol, lauric acid, myristic acid, palmitic acid, stearic acid, isostearic acid, oleic acid, mineral oil, petrolatum, cottonseed oil, coconut oil, sesame seed oil, peanut oil, isopropyl myristate, isopropyl palmitate, gelatin, albumin, dextrose, poly(ethylene glycol), poly(ethylene oxide), poly(vinylpyrrolidone), hydroxypropyl methyl cellulose, water soluble cellulose based polymers, hyaluronic acid, heparin, heparin sulfate, poly(vinyl alcohol), sialic acid, chitosan, gamma globulin, albumin, homopolymers and copolymers (and homo-oligomers and co-oligomers) of acrylamide, homopolymers and copolymers (and homo-oligomers and co-oligomers) of acrylic acid, homopolymers and copolymers (and homo-oligomers and co-oligomers) of maleic acid, homopolymers and copolymers (and homo-oligomers and co-oligomers) of vinyl acetate, homopolymers and copolymers (and homo-oligomers and co-oligomers) of crotonic acid, vinylimidazole, homopolymers and copolymers (and homo-oligomers and co-oligomers) of maleic anhydride, and homopolymers and copolymers (and homo-oligomers and co-oligomers) of vinylpyrrolidone;
wherein the surfactant(s) are independently selected from the group consisting of sorbitan oleate, sorbitan laurate, phospholipids, albumin, gelatin, lecithin, random and block copolymers of polyethylene oxide and polypropylene oxide, diblock copolymers and co-oligomers of polyethylene oxide and polypropylene oxide, triblock copolymers of polyethylene oxide and polypropylene oxide, Poloxamer 407, polyvinyl alcohol, polysorbate 20, polysorbate 60, polysorbate 80, polyoxyethylene sorbitan oleates, polyoxyethylene sorbitan laurates, polyethylene glycol p-(1,1,3,3-tetramethylbutyl)-phenyl ether, palmitate-co-polyethylene glycol, Vitamin E TGPS, ascorbyl palmitate, phosphatidylcholine, polyethylene glycol-phosphatidyl ethanolamine conjugate (PEG-PE), fatty acid esters, glycerol monostearate, sodium dodecyl sulfate (SDS), cellulose acetate, and didodecyldimethyl ammonium bromide (DMAB).

22. A method of treating, preventing, or ameliorating a vascular disease, a vascular disorder, or both, in a diabetic or pre-diabetic patient, the method comprising:
   delivering a drug coated balloon to a vascular region of a patient and expanding the drug coated balloon to release the drug of the drug coated balloon at the vascular region.
   delivering a stent to, and deploying the stent at the vascular region of the patient; and
   prior to, during, or both prior to and during the deployment of the stent, administering a lubricant formulation to the vascular region of the patient;
   wherein the patient is identified as having a diabetic condition or a pre-diabetic condition;
   wherein the patient is in need of treating, preventing, or ameliorating a vascular disease, a vascular disorder, or both;
   wherein the expansion of the drug coated balloon occurs prior to the administration of the lubricant formulation and prior to the deployment of the stent; and
   wherein the lubricant formulation comprises
      at least carboxymethylcellulose;
      or
      at least one surfactant selected from the group consisting of diblock copolymers and co-oligomers of polyethylene oxide-co-polypropylene oxide, triblock copolymers of polyethylene oxide-co-polypropylene oxide, polyvinyl alcohol, polysorbate 60, and palmitate-co-polyethylene glycol;
      or
      at least carboxymethylcellulose; and at least one surfactant selected from the group consisting of diblock copolymers and co-oligomers of polyethylene oxide-co-polypropylene oxide, triblock copolymers of polyethylene oxide-co-polypropylene oxide, polyvinyl alcohol, polysorbate 60, and palmitate-co-polyethylene glycol;
   and
   wherein the lubricant formulation is a fluid that is free of drugs, wherein said drugs do not include said carboxymethylcellulose and said surfactants of the lubricant formulation.

* * * * *